United States Patent
Anderson (10) Patent No.: US 11,351,116 B2
(45) Date of Patent: Jun. 7, 2022

(54) COMPOSITIONS AND METHODS FOR TREATING SKIN CONDITIONS

(71) Applicant: Aqua Regenerative Therapies LLC, San Diego, CA (US)

(72) Inventor: Sean Matthew Anderson, San Diego, CA (US)

(*) Notice: Subject to any disclaimer, the term of this patent is extended or adjusted under 35 U.S.C. 154(b) by 188 days.

(21) Appl. No.: 16/049,777

(22) Filed: Jul. 30, 2018

(65) Prior Publication Data

US 2018/0333356 A1  Nov. 22, 2018

Related U.S. Application Data (62) Division of application No. 14/923,258, filed on Oct. 26, 2015, now Pat. No. 10,034,834.

(Continued)

(51) Int. Cl.
| | |
|---|---|
| *A61K 9/06* | (2006.01) |
| *A61K 8/06* | (2006.01) |
| *A61K 8/73* | (2006.01) |
| *A61K 9/00* | (2006.01) |
| *A61K 9/107* | (2006.01) |

(Continued)

(52) U.S. Cl.
CPC .............. *A61K 9/06* (2013.01); *A61K 8/0291* (2013.01); *A61K 8/064* (2013.01); *A61K 8/25* (2013.01); *A61K 8/26* (2013.01); *A61K 8/37* (2013.01); *A61K 8/73* (2013.01); *A61K 8/731* (2013.01); *A61K 8/735* (2013.01); *A61K 8/8152* (2013.01); *A61K 8/894* (2013.01); *A61K 8/927* (2013.01); *A61K 9/0014* (2013.01); *A61K 9/1075* (2013.01); *A61K 9/7015* (2013.01); *A61Q 19/00* (2013.01); *A61Q 19/007* (2013.01);

(Continued)

(58) Field of Classification Search
None
See application file for complete search history.

(56) References Cited

U.S. PATENT DOCUMENTS

| | | | | |
|---|---|---|---|---|
| 6,417,237 B1 * | 7/2002 | Dadey | ..................... | A61P 25/00 424/486 |
| 2005/0079145 A1 * | 4/2005 | Constantinides | ....... | A61P 13/08 424/70.11 |

(Continued)

FOREIGN PATENT DOCUMENTS

EP  2151231 B1 *  8/2017  .............. A61Q 19/00

OTHER PUBLICATIONS

Constantinides, P. P., et al., Formulation and Instestinal Absorption Enhancement Evaluation of Water-in-Oil Microemulsions Incorporating Medium-Chain Glycerides, Pharm. Res. 11(10) pp. 1385-1390 (1994); hereinafter, "Constantinides I." (Year: 1994).*

(Continued)

*Primary Examiner* — Dominic Lazaro
(74) *Attorney, Agent, or Firm* — Alpine IP (57) ABSTRACT

Methods for forming dermatological compositions that deliver water and/or other hydrophilic compounds into or through the dermis using reverse micelles. The methods include forming compositions with an oil-based continuous phase and an emulsifier that form nanoparticle micelles. The nanoparticle micelles are formulated into biocompatible topical ointments that are stable at room temperature and can be distributed in consumer packaging and consumer distribution channels.

19 Claims, 3 Drawing Sheets

Related U.S. Application Data

(60) Provisional application No. 62/068,623, filed on Oct. 24, 2014.

(51) Int. Cl.
*A61Q 19/00* (2006.01)
*A61K 8/02* (2006.01)
*A61K 47/36* (2006.01)
*A61K 8/37* (2006.01)
*A61K 8/26* (2006.01)
*A61K 8/81* (2006.01)
*A61K 8/25* (2006.01)
*A61K 9/70* (2006.01)
*A61K 8/92* (2006.01)
*A61K 8/894* (2006.01)

(52) U.S. Cl.
CPC ...... *A61K 2800/21* (2013.01); *A61K 2800/49* (2013.01); *A61K 2800/82* (2013.01)

(56) References Cited

U.S. PATENT DOCUMENTS

2005/0191343 A1* 9/2005 Liang .................... A61K 47/10
424/450
2010/0247563 A1* 9/2010 Hines ................... A61K 36/736
424/195.16

OTHER PUBLICATIONS

English language translation of EP 2 151 231 B1 (2010). (Year: 2010).*

* cited by examiner

COMPOSITIONS AND METHODS FOR TREATING SKIN CONDITIONS

CROSS-REFERENCE TO RELATED APPLICATIONS

This application is a divisional of U.S. patent application Ser. No. 14/923,258, filed Oct. 26, 2015, which claims the benefit of, and priority to U.S. Provisional Patent Application Ser. No. 62/068,623, filed Oct. 24, 2014, the entire contents of which is incorporated by reference herein.

BACKGROUND OF THE INVENTION

1. The Field of the Invention

The present invention relates to methods for treating low-grade inflammatory skin conditions and methods for making the compositions and treating subjects with inflammatory skin conditions.

2. Background of the Invention

Inflammation of the skin (dermatitis) in mammals can result from a number of different etiologies. Dermatitis can be caused by eczema, in particular atopic eczema (atopic dermatitis), disseminated neurodermatitis, flexural eczema, infantile eczema, prurigo diathsique, contact dermatitis, (eg irritant contact dermatitis, allergic contact dermatitis and photocontact dermatitis), xerotic eczema, seborrheic eczema, dyshidrosis, discoid eczema, venous eczema, dermatitis herpetiformis, neurodermatitis and autoeczematisation. Dermatitis can also be caused by skin inflammation resulting from exposure to radiation, in particular exposure to ultraviolet radiation or other conditions resulting in rosacea.

Inflammation of the skin causes rashes, redness, skin edema (swelling), itching, blistering, sensations of pain and/or heat and can be unsightly. The itchiness caused by inflammation can lead to scratching. Scratching of skin that is already damaged in some way can easily lead to the barrier of the epidermis being broken, resulting in bleeding, and secondary infection with pathogens. Such secondary infection can require treatment with antibiotics.

The most common form of treatment for skin conditions are topical lotions. Lotions tend to provide minimal and temporary relief. More effective relief from skin conditions can be achieved using oral and/or topical steroids. There are, however, drawbacks associated with steroid treatments. Common side effects associated with current steroid treatments include stunted growth, thinning of the skin, muscle loss, and osteoporosis.

SUMMARY

The present invention relates to dermatological compositions and related methods for treating skin conditions using reverse micelle nanoparticles. The compositions are formulated into a dermatological ointment suitable for being stored and dispensed onto the skin.

The compositions include reverse micelles stably dispersed in an oil-based continuous phase (i.e., a water in oil emulsion). The reverse micelles include an emulsifier and an aqueous component (i.e., water) and optionally one or more hydrophilic components such as humectants and/or water-soluble pharmaceutical agents. The molecular weight of the emulsifier may be selected to facilitate transdermal delivery of the hydrophilic component. In one embodiment the emulsifier may have a molecular weight less than 2 kDa. For example, non-ionic emulsifiers such as polysorbates and sorbitans have been found to be effective for achieving transdermal delivery of the hydrophilic component.

The reverse micelles are also manufactured to have a sub micron particle size. In one embodiment, the reverse micelles have a median particle size less than 800 nm, preferably less than 500 nm or 250 nm. Reverse micelle nanoparticles can be formed by properly selecting and mixing the oil component, emulsifier, and aqueous component. In some embodiments, stable reverse micelles are formed using sonication.

The dermatological compositions described herein are engineered to deliver water and/or a hydrophilic component into and/or through the dermis of the skin. This is in contrast to the vast majority of topical dermatological compositions, which use an oil-in-water emulsion. Oil-in-water emulsions have an aqueous continuous phase, which holds the oil component on the surface of the skin. As the aqueous phase evaporates the oil deposits on the skin as a protective film, which prevents dermal moisture from escaping. However, the most effective films require a layer of oil that makes the skin feel greasy, which is undesirable for most people. While traditional dermatological compositions can impede dermal moisture from escaping, these compositions are generally ineffective at imbuing the skin with moisture or hydrophilic compounds. Attempts to remedy the problem by adding penetrating agents have failed to achieve meaningful transdermal delivery in traditional dermatological compositions.

Applicant has found that by forming nano-sized reverse micelles dispersed in a continuous oil phase, the water can serve as a compartment to deliver a hydrophilic component into and/or through the dermis. Applicant's experimental data illustrates the importance of both the reverse micelle (i.e., water in oil emulsion) and particle size to achieving transdermal delivery (see Examples).

BRIEF DESCRIPTION OF THE DRAWINGS

To further clarify the above and other advantages and features of the present invention, a more particular description of the invention will be rendered by reference to specific embodiments thereof which are illustrated in the appended drawing. It is appreciated that this drawing depicts only illustrated embodiments of the invention and is therefore not to be considered limiting of its scope. The invention will be described and explained with additional specificity and detail through the use of the accompanying drawing in which.

DETAILED DESCRIPTION

I. Introduction

The dermatological compositions of the present invention include an oil component, an aqueous component, an emulsifier, and optionally one or more of a hydrophilic component, preservatives, active agents, propellants, purging gases, buffers or salts, viscosity modifiers, or other agents such as fragrances. The concentrations of the aqueous component, oil component, and emulsifier are selected and mixed in combination with the other components to form nano-sized reverse micelles in a continuous oil phase. The emulsion is formulated into an ointment that is suitable for application to the skin of a person and stable at room temperature. The compositions can be stored in consumer packaging and dispensed by a consumer for treatment of skin conditions such as dry skin.

II. Components Used to Manufacture the Dermatological Compositions

1. Oil Component

The oil component includes one or more lipophilic compounds suitable for use as a continuous oil phase in forming reverse micelles (i.e., a water-in-oil emulsion). The oil component preferably includes at least one of a fatty acid hydrocarbon, ester hydrocarbon, an acylglycerol, mineral oil, oils of natural or synthetic origin, phosphoglycerides, sphingolipids, waxes, aliphatic alcohol, or saturated, mono-unsaturated, and/or poly-unsaturated straight chain or branched hydrocarbons. The forgoing compounds may have greater than or equal to 8, 11, or 13 carbons and less than or equal to 24, 20, or 18. The oils may be petroleum based or plant based.

Suitable compounds that can be used in the oil component include, but are not limited to, caprylic/capric triglycerides; steareth-2; steareth-21; polyglyceryl-3 beeswax; a branched-carboxylic acid ester of a branched-chain alcohol selected from the group consisting of isononyl isononanoate, isodecyl isononanoate, isooctyl isononanotate, isooctyl isooctanoate, isononyl isooctanoate, isodecyl isooctanoate, isononyl isodecanoate, isooctyl isodecanoate, and isodecyl isodecanoate; an acrylates/$C_{10}$-$C_{30}$ alkyl acrylates crosspolymer; methylgluceth-20; a glyceryl ester of a long chain fatty acid selected from the group consisting of glyceryl monostearate, glyceryl monopalmitate, and glyceryl monoarachidate; hydrogenated vegetable oil; hydrocarbon-based materials such as petrolatum; silicone-based materials (both non-volatile and volatile) such as cyclomethicone, dimethiconol, dimethicone, and dimethicone copolyol; squalane; $C_{12}$-$C_{15}$ alkyl benzoates; di-$C_{12}$-$C_{15}$ alkyl fumarate; cholesterol; lanolin, lanolin alcohol, lanoline derivatives; octyldodecanol, isostearic acid; a branched-chain neopentanoate selected from the group consisting of octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate; an arachidyl ester of a short-chain carboxylic acid selected from the group consisting of arachidyl propionate, arachidyl acetate, arachidyl butyrate, and arachidyl isobutyrate; a long-chain fatty acid ester of a medium-chain alcohol selected from the group consisting of ethylhexyl palmitate (octyl palmitate), octyl myristate, octyl stearate, heptyl palmitate, heptylmyristate, heptyl stearate, nonyl palmitate, nonyl myristate, and nonyl stearate; oleyl erucate; jojoba oil; a myristyl ester of a long-chain fatty acid selected from the group consisting of myristyl myristate, myristyl laurate, and myristyl palmitate; bisabolol; hydrogenated jojoba oil; jojoba esters; methyl-gluceth-20 sesquistearate; PPG-14 butyl ether; PPG-15 stearyl ether; PPG-1-isoceteth-3-acetate; laureth-2-benzoate; diisostearyl dimmer dilinoleate; a long-chain cis-monounsaturated fatty acid ester of a medium-chain alcohol; a medium-chain saturated carboxylic acid ester of a long-chain alcohol; hydrogenated soy glycerides; a long-chain fatty acid ester of cetyl alcohol selected from the group consisting of cetyl palmitate, cetyl stearate, and cetyl myristate; palm kernel oil; palm oil; and an arachidyl ester such as arachidyl acetate, arachidyl propionate, arachidyl butyrate, or arachidyl isobutyrate; panthenol; isostearyl neopentanoate; isocetyl stearate; octyl dodecanol; phenyl trimethicone; cyclomethicone; dimethiconol; safflower oil; *Theobroma grandiflorum* seed butter; sunflower seed oil; shea butter; ceramides ceramide 2 or ceramide 3), oleyl alcohol, oleic acid, stearic acid, dicaprylate/dicaprate, diethyl sebacate, isostearyl alcohol, pentylene glycol, isononyl isononanoate, polyquarternium-10 (quaternized hydroxyethyl cellulose), camellia oleifera leaf extract, phytosteryl canola glycerides, caprylic/capric triglycerides, punica granatum sterols, ethylhexyl stearate, betaine, behenyl alcohol (docosanol), stearyl alcohol (1-octadecanol), *laminaria ochroleuca* extract, behenic acid, caproyl sphingosine, caproyl phytosphingosine, dimethicone-divinyldiethicone-silsesquioxane crosspolymer, In a preferred embodiment, the oil component includes a fatty acid hydrocarbon, an ester hydrocarbon, an ether hydrocarbon, or a combination of these. Preferred fatty acid hydrocarbons include oleic acid, stearic acid, linoleic acid, or linolenic acid. Examples of preferred ester compounds include oleyl ester, oleic ester, linoleic ester, or linolenic ester. Preferred ether hydrocarbons include oleyl ether, oleic ether, linoleic ether, or linolenic ether. The R group of the ester or ether may be a branched or un-branched hydrocarbon with 1-20 carbons.

2. Emulsifiers

Many dermatological compositions contain chemical emulsions which use surface active ingredients to disperse dissimilar chemicals in a particular solvent system. For example, most aqueous components do not uniformly disperse in lipid-like (oily or fatty) or lipophilic ingredients unless they are first combined with emulsifiers, which form microscopic aqueous soluble structures (droplets) that contain a hydrophilic interior and a lipophilic exterior, resulting in a water-in-oil emulsion. In order to be soluble in a lipid phase, a molecule must be non-polar or non-charged so as to favorably interact with lipid molecules, which are also non-polar.

Such emulsions can be destabilized by the addition of salts or other charged ingredients, which can interact with the polar or charged portions of the emulsifier within an emulsion droplet. Emulsion destabilization results in the aqueous and lipophilic ingredients separating into two layers, potentially destroying the commercial value of a dermatological product.

Emulsifiers suitable for use in the present invention may be ionic or non-ionic. Nonionic is preferred. These include, but are not limited to: sodium isostearate, cetyl alcohol, polysorbates (Polysorbate 20, Polysorbate 40, Polysorbate 60, Polysorbate 80), sorbitans including span 20, 40, 60, 80, 83, 85, and 120 (sorbitan monolaurate, sorbitan monopalmitate, sorbitan monostearate, sorbitan monooleate, sorbitan sesquioleate, sorbitan trioleate, sorbitan isostearate) and tween 20, 21, 40, 60, 61, 65, 80 (PEG-20 sorbitan monolaurate, PEG-4 sorbitan monolaurate, PEG-20 sorbitan monopalmitate, PEG 20 sorbitan monostearate, PEG-4 sorbitan monostearate, PEG-20 sorbitan tristearate, PEG-20 sorbitan monooleate), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate ceteth-10 is the polyethylene glycol ether of cetyl alcohol where n has an average value of 10; ceteth-10 phosphate is a mixture of phosphoric acid esters of ceteth-10), ceteth-20, Brij S10 (polyethylene glycol octadecyl ether, average $M_n$~711), PEG-20 phytosterol, and Poloxamers. Appropriate combinations or mixtures of such emulsifiers may also be used according to the present invention.

Other suitable emulsifiers for use in the formulations of the present invention include, but are not limited to, *glycine soja* protein, sodium lauroyl lactylate, polyglyceryl-4 diisostearate-polyhydroxystearate-sebacate, behentrimonium methosulfate-cetearyl alcohol, non-ionic emulsifiers like emulsifying wax, polyoxyethylene oleyl ether, PEG-40 stearate, carbomer, cetostearyl alcohol (cetearyl alcohol), ceteareth-12, ceteareth-20, ceteareth-25, ceteareth-30, ceteareth alcohol, Ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, and PEG-100 stearate, ceramide 2, ceramide 3, stearic acid, cholesterol, laureth-12, steareth-2, and steareth-20, or combinations/mixtures thereof, as well as cationic emulsifiers like stearamidopropyl dimethylamine and behentrimonium methosulfate, or combinations/mixtures thereof.

The molecular weight of the emulsifier is preferably less than 10 kDa, 5 kDa, or 2 kDa and/or greater than 100 Da, 250 Da, or 500 Da or in a range of any of the foregoing endpoints.

3. Aqueous Component

The compositions include an aqueous component. The aqueous component provides the bulk liquid for the interior portion of the micelles. The aqueous component serves as a compartment or carrier into which the hydrophilic components can be dissolved. The aqueous component is typically water.

4. Hydrophilic Components

The compositions of the invention may include a hydrophilic component dissolved into the aqueous phase of the micelles (i.e., the aqueous component). The hydrophilic component may be any water-soluble compound that can be caused to partition into the aqueous phase of the reverse micelles. Examples of suitable materials that can be used as a hydrophilic component include, but are not limited to, humectants, emollients, water-soluble plant extracts, water-soluble active agents such as pharmaceutical agents, and combinations of these. In some embodiments, the hydrophilic component may also be substantially free of certain hydrophilic molecules. For example, in some embodiment, the compositions of the invention are substantially free of low molecular weight alcohols such as methanol, ethanol, propanol, or butanol.

4.1 Humectants and Emollients

The hydrophilic component may include water soluble humectants and emollients that dissolve in the aqueous phase and are delivered to the dermis. Humectants can include glycols, glycosaminoglycans such as hyaluronan, glycerol, liquid polyols, or dimethyl sulfoxide. In one embodiment, the hydrophilic component can include a glycol selected from ethylene glycol, butyl ene glycol, isoprene glycol, propyl e glycol).

In a preferred embodiment, the composition may include hyaluronan. The hyaluronan may be hyaluronic acid or salts thereof (e.g., sodium hyaluronate), sodium hyaluronate crosspolymer, hydrolyzed hyaluronic acid, sodium butyroyl-formoyl hyaluronate. The hyaluronan preferably has a molecular weight greater than 3, 5, 10, or 15 kDa and less than 100, 50, or 15 kDa, or within a range of any of the foregoing upper and lower molecular weights. In some embodiments, the hyaluronan is provided as a polymeric material that is formed into particles of a desired size. In other embodiments, the hyaluronan may be provided as a particulate.

Other suitable humectants or emmolients include polyglutamic acid, tetradecyl aminobutyroylvalylaminobutyric urea trifluoroacetate, *micrococcus* lysate, hydrolyzed rice bran protein, *glycine soja* protein, and 1,3-bis(N-2-(hydroxyethyl)palmitoylamino)-2-hydroxypropane, hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane.

4.2. Water-Soluble Active Agents

The active agent may be any water-soluble material that has a desired effect when applied topically to a mammal, particularly a human. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, anti protozoal agents, anti-oxidants, antihistamines, vitamins, and hormones. Mixtures of any of these active agents may also be employed. Additionally, dermatologically-acceptable salts and esters of any of these agents may be employed. In some embodiments, the active agent is a water-soluble active agent that is dissolved in the hydrophilic component of the reverse micelles.

4.3 Antibiotics

Representative antibiotics include, without limitation, benzoyl peroxide, alfa terpineol, octopirox, erythromycin, zinc, tetracyclin, triclosan, azelaic acid and its derivatives, phenoxy ethanol and phenoxy propanol, ethyl acetate, clindamycin (e.g., clindamycin phosphate) and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin. Mixtures of these antibiotic agents may also be employed. Additionally, dermatologically-acceptable salts and esters of any of these agents may be employed.

4.4 Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac, fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone; and niacinamide. Mixtures of these non-steroidal anti-inflammatory agents may also be employed, as well as the dermatologically acceptable salts and esters of these agents. For example, etofenamiate, a flufenamic acid derivative, is particularly useful for topical application.

4.5 Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone; dexamethasone-phosphate, beclomethasone dipropionate, clobetasol valerate, desonide, desoxynietha-sone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone; fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters (including betamethasone dipropionate), chloroprednisone, chlorprednisone acetate, eloconelone, elescinolone, dichlorisone, diflurprednate, flucloronide, flunisolide, fluoromethalone, fluperolone, fluprednisolone, hydrocortisone valerate; hydrocortisone cyclopentylpropionate, hydrocortamate, meprednisone, paramethasone, prednisolone, prednisone, beclomethasone dipropionate, triamcinolone, and mixtures thereof.

4.6 Anesthetics

Suitable anesthetics include the aminoacylanilide compounds such as lidocaine, prilocalne, bupivacaine, levobupivacaine, ropivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, butamben, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amide compounds such as dibucaine and related local anesthetic compounds; aminoketone compounds such as falicaine, dyclonine and related local anesthetic compounds; and amino ether compounds such as pramoxine, dimethisoquien, and related local anesthetic compounds; and para-amino benzoic acid esters such as benzocaine. Other suitable local anesthetics include ketocaine, dibucaine, amethocaine, propanacaine, and propipocaine.

4.7 Antimicrobial Agents

Suitable antimicrobial agents include, but are not limited to, antibacterial, antifungal, antiprotozoal and antiviral agents; such as beta-lactam drugs; quinolone drugs, ciprofloxacin, norfloxacin, tetracycline, erythromycin, amikacin, triclosan, doxycycline, capreomycin, chlorhexidine, chlortetracycline, oxytetracycline, clindamycin (e.g., clindamycin phosphate), ethambutol, metronidazole, pentamidine, gentamicin, kanamycin, lineomycin, methacycline; methenamine, minocycline, neomycin, netilmicin, streptomycin, tobramycin, and miconazole. Also included are tetracycline hydrochloride, framesol, erythromycin estolate, erythromycin stearate (salt), amikacin sulfate, doxycycline hydrochloride, chlorhexidine gluconate, chlorhexidine hydrochloride; chlortetracycline hydrochloride, oxytetracycline hydrochloride; clindamycin hydrochloride, clindamycin phosphate, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

4.8 Keratolytic Agents

Suitable keratolytic agents include, but are not limited to, urea, salicylic acid, papain, bromelain, sulfur, glycolic acid, pyruvic acid, resorcinol, N acetylcysteine, mandelic acid, retinoids such as retinoic acid (e.g., tretinoin) and its derivatives (e.g., cis and trans, esters), retinol, alpha hydroxy acids, beta hydroxy acids, coal tar, and combinations thereof.

4.9 Plant Extracts

Other suitable water soluble active agents include plant extracts, such as extracts from *Euterpe oleracea, Aloe vera, Arnica montana, Saraca indica, Euphorbia hirta, Astragalus propinquus, Berberis vulgaris, Atropa belladonna, Vaccinium myrtillus, Momordica charantia, Veronia amygdalina, Citrus aurantium, Actaea racemosa, Cnicus benedictus*, genus *Vaccinium, Arctium lappa, Uncaria tomentosa, Capsicum annuum, Apium graveolens, Matricaria recutita, Anthemis nobilis, Larrea tridentate, Vitex agnus-castus, Capsicum frutescens, Cinchona, Syzygium aromaticum, Cassia occidentalis, Symphytum officinale, Vaccinium macrocarpon, Taraxacum officinale, Digitalis lanata, Angelica sinensis, Sambucus nigra, Ephedra sinica, Eucalyptus globulus, Viscum album*, evening primrose, fenugreek, feverfew, linum; *Usitatissimum, Allium sativum, Zingiber officinale, Ginkgo biloba, Ginseng, Hydrastis canadensis, Vitis vinifera, Psidium guajava, Hathorn, Lawsonia inermis, Hoodia gordonii, Aesculus hippocastanum, Equisetum arvense, Piscidia erythina, Piper methysticum, Amorphophallus konjac, Kratom, Sceletium tortuosum*, lavender, lemon, licorice root, *Nelumbo nucifera, Calendula officinalis, Althaea officinalis, Moringa oleifera, Silybum marianum, Azadirachta indica, Morinda citrifolia, Papaver somniferum, Origanum vulgare, Carica papay, Menthe piperita, Echinacea purpurea, Passiflora, Trifolium pretense, Rosmarinus officinalis, Salvia officinalis, Peganum harmala, Hypericum perforatum, Serenoa repens, Satureja hortensis, Melaleuca alternifolia, Tripeterygium wilfordii, Thymus vulgaris, Ocimum tenuiflorum, Curcuma longa, Pelargonium sidoides, Valeriana officinalis, Salix alba*, and *Eriodictyon crassifolium*.

4.10 Miscellaneous Water Soluble Active Agents

Other hydrophilic components include growth factors (such as VEGF, NGF, TGF, EGF, PDGF, hsp90, and the like) and fragments thereof; extracellular matrix protein components such as collagen, fibronectin, vitronectin, and fragments thereof; glycosaminoglycans such as heparin, heparan sulfate, chitosan, alginate, hyaluronic acid, and fragments thereof; peptides and peptide fragments; peptide-carbohydrate conjugates; deoxyribonucleic acid; ribonucleic acid;

hydrophilic polymers such as polyethyleneimine, polyethylene glycol, and poly-N-isopropylacrylamide.

Those skilled in the art will recognize that the selection of the hydrophilic component can depend in part on the selection of the emulsifier and/or oil component. The interaction of the emulsifier, hydrophilic component, and oil component can influence which phase a particular compound will partition into and therefore can change whether a particular compound will function as an emulsifier, oil component or hydrophilic component. Thus, the foregoing lists of emulsifiers, oil components and hydrophilic components are not necessarily mutually exclusive.

5. Preservatives and Antioxidants

The composition may further include components adapted to improve the stability of the reverse micelle or the effectiveness of the applied formulation. In particular, preservatives can be used to provide a suitable shelf life at room temperature for selling and/or distributing the composition to consumers.

Suitable preservatives for use in the present invention include, but are not limited to: caprylhydroxamic acid; propanediol; methyl propanedial; glyceryl caprylate; glycerin; parabens; lauric acid; ureas, such as imidazolidinyl urea and diazolidinyl urea; chlorphenesin; methylisothiazolinone; phenoxyethanol; sodium methyl paraben, methylparaben, ethylparaben, and propylparaben; ethyl hexyl glycerin; potassium sorbate; sodium benzoate; sorbic acid; benzoic acid; caprylyl glycol; hexylene glycol; formaldehyde; phytosphingosine; citric acid; sodium citrate; zinc citrate; chlorine dioxide; quaternary ammonium compounds, such as benzalkoniutn chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, superoxide dismutase, oxidoreductases, *Arabidopsis thaliana* extract, chrysin, black raspberry seed oil, raspberry seed oil, pomegranate seed oil, cranberry seed oil, sodium ascorbate/ascorbic acid, ascorbyl palmitate, propyl gallate, and chelating agents like EDTA. (e.g., disodium EDTA), citric acid, and sodium citrate.

In certain embodiments, the antioxidant or preservative comprises (3-(4-chlorophenoyx)-2-hydroxypropyl)carbamate.

In certain embodiments, antioxidants or preservatives of the present invention may also function as a moisturizer or emollient, for example.

In addition, combinations or mixtures of these preservatives or anti-oxidants may also be used in the formulations of the present invention.

6. Propellants

In certain embodiments, the emulsion includes a propellant. The propellant may be a HFA or a mixture of one or more hydrofluorocarbons. Suitable hydrofluorocarbons include 1,12-tetrafluoroethane (HFA 134a); 1,1,2,3,3,3-heptafluoropropane (HFA 227); and mixtures and admixtures of these and other HFAs that are currently approved or may, become approved for medical use are suitable. The concentration of the HFA propellant is about 2% to about 50% by weight of the composition. In certain embodiments, the propellant comprises a hydrofluoroolefin (HFO), or a mixture of HFO and HFA. Suitable hydrofluoroolefins include 1,3,3,3-tetrafluoropropene (FIFO 1234ze) and mixtures and admixtures of this and other HFO suitable for topical use. The concentration of the HFO propellant is about 2% to about 50% by weight of the composition. Hydrocarbon as well as CFC propellants can also be used in the present invention.

7. Purging Gases

In one embodiment, the air in the container charged with the composition is replaced by an inert gas. In certain embodiments, the inert gas is selected from the group consisting of argon, nitrogen, and mixtures thereof.

8. Buffer Salts

Suitable buffer salts are well-known in the art. Examples of suitable buffer salts include, but are not limited to sodium citrate, citric acid, sodium phosphate monobasic, sodium phosphate dibasic, sodium phosphate tribasic, potassium phosphate monobasic, potassium phosphate dibasic, and potassium phosphate tribasic.

9. Viscosity Modifiers

Suitable viscosity adjusting agents (i.e., thickening and thinning agents or viscosity modifying agents) for use in the formulations of the present invention include, but are not limited to, protective colloids or non-ionic gums such as hydroxyethyiceliulose, xanthan gum, and *sclerotium* gum, as well as magnesium aluminum silicate, silica, microcrystalline wax, beeswax, paraffin, and cetyl palmitate. Crosspolymers of acrylates/$C_{10-30}$ alkyl acrylate are also considered. In addition, appropriate combinations or mixtures of these viscosity adjusters may be utilized according to the present invention.

10. Additional Constituents

Additional constituents suitable for incorporation into the emulsions of the present invention include, but are not limited to: skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, immunomodulators, and pH adjusters (e.g., citric acid, sodium hydroxide, and sodium phosphate).

Examples of peptides that interact with protein structures of the dermal-epidermal junction include palmitoyl di peptide-5 diaminobutyloyl hydroxythreonine, palmitoyl tripeptide-5, acetyl octapeptide-3, pentapeptide-3, palmitoyl dipeptide-5 diaminohydroxybutyrate, dipeptide diaminobutyroyl benzylamide diacetate, palmitoyl tetrapeptide-7, palmitoyl oligopeptide, and palmitoyl dipeptide-6 diaminohydroxybutyrate.

Examples of skin soothing agents include, but are not limited to algae extract, mugwort extract, stearyl glycyrrhetinate, bisabolol, allantoin, aloe, avocado oil, green tea extract, hops extract, chamomile extract, colloidal oatmeal, calamine, cucumber extract, and combinations thereof.

N-hydroxysuccinimide activates the elimination of blood originated pigments responsible for dark color and inflammation that causes under eye circles.

In certain embodiments, the compositions comprise bergamot or bergamot oil. Bergamot oil is a natural skin toner and detoxifier. In certain embodiments, it may prevent premature aging of skin and may have excellent effects on oily skin conditions and acne.

Examples of vitamins include, but are not limited to, vitamins A, D, E, K, and combinations thereof. Vitamin analogues are also contemplated; for example, the vitamin D analogues calcipotriene or calcipotriol.

In certain embodiments, the vitamin may be present as tetrahexyldecyl ascorbate. This compound exhibits antioxidant activity, inhibiting lipid peroxidation. In certain embodiments, use can mitigate the damaging effects of UV exposure. Studies have shown it to stimulate collagen production as well as clarifying and brightening the skin by inhibiting melanogenesis (the production of pigment) thereby promoting a more even skin tone.

Examples of sunscreens include, but are not limited to, p-aminobenzoic acid, avobenzone; cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, benzoate, octyl triazone, diethylhexyl butamido triazone, polysilicone-15, and combinations thereof.

Suitable fragrances and colors may be used in the formulations of the present invention. Examples of fragrances and colors suitable for use in dermatological products are known in the art.

Suitable immunomodulators include, but are not limited to, tetrachlorodecaoxide, deoxycholic acid, tacrolimus, pimecrolimus, and beta-glucan.

In certain embodiments, palmitoyl-lysyl-valyl-lysine bis-trifluoroacetate is added. This peptide stimulates collagen synthesis in human fibroblasts.

In certain embodiments, plant extracts may be included. Examples include *Artemisia vulgaris* extract, plankton extract, *Chlorella vulgaris* extract, and phytosterol.

An example of a film-forming agent is polysilicone-11.

Often, one constituent of a composition may accomplish several functions. In one embodiment, the present invention relates to constituents that may act as a lubricant, an emollient, or a skin-penetrating agent. In one embodiment, the multi-functional constituent is isocetyl stearate, isopropyl isostearate, isopropyl palmitate, or isopropyl myristate.

III. Methods for Manufacturing Dermatological Compositions

Embodiments of the invention relate to making dermatological compositions of a water-in-oil emulsion suitable for delivering water and/or a hydrophilic component into or through the dermis of the skin. The dermatological compositions may be manufactured by forming a precursor composition and mixing the precursor composition to yield reverse micelles in a biocompatible ointment suitable for being applied to a person's skin.

The compositions are formed by selecting appropriate concentrations of a oil component, an emulsifier, an aqueous component, and other constituents such as a hydrophilic component or preservative and mixing the components together to form reverse micelles. The emulsifier and its concentration are selected to exceed the critical micelle concentration. In some embodiments, forming micelles that can penetrate into the dermis includes selecting at least one emulsifier having a molecular weight less than 2 kDa. Preferably the emulsifier is nonionic.

The continuous phase (i.e., oil component) may have a concentration of greater than or equal to 15%, 20%, 25% and/or less than or equal to 90%, 80%, 60%, or 40% or within a range of the foregoing. The emulsifier may be included in a concentration of greater than or equal to 2%, 3%, 4%, 5%, and/or less than or equal to 20%, 15%, 30%. The aqueous component may be included in a concentration greater than or equal to 5%, 10%, %15, or 20% and/or less than 80%, 60%, 40%, or 20% or within a range of any of the foregoing endpoints. The hydrophilic component may be included in a concentration of at least 0.05%, 0.1%, or 0.2%, or 0.4% and/or less than or equal to 2%, 1.5%, 1.0%, or 0.7%, or within a range of the foregoing. Other components that make up the balance of the composition (e.g., pH modifiers, thickeners, etc.) may be used in concentrations that cumulatively are greater than 0.5%, 1%, or 2% and/or less than or equal to 10%, 5%, 3%, or 2%, or within a range of the foregoing.

The precursor composition is then mixed to form micelles. The mixing is carried out for a sufficient time that the emulsification nears completion (i.e., the concentration of micelles is near a maximum). Typically the majority of the aqueous component will be emulsified. The amount of mixing typically depends on the volume of the mixture. The mixing time may be greater than or equal to 10 seconds, 30 seconds, 1 minute, or 5 minutes and less than 20 minutes, 10 minutes, or 5 minutes or within a range of the foregoing. Typically, smaller volumes (e.g., less than 1 liter) tend to require shorter periods of mixing time and larger batches (e.g., greater than 10 liters requires longer mixing times).

In one embodiment, the mixing includes sonication. Sonication has been found to be surprisingly effective at forming micelles that will deliver hydrophilic materials into and/or through the dermis.

The dermatological compositions also include a preservative to give the composition suitable shelf life at room temperature for use in consumer applications. The preservative may have a concentration of greater than or equal to 0.05%, 0.1%, or 0.2% and/or less than or equal to 5%, 3%, or 2%, or within a range of the foregoing. The preservative may be selected in combination with the lipophilic compounds of the oil component and the emulsifier to produce a stable composition for a period of greater than or equal to 10 days, 30 days, 60 days, or one year.

The shelf life allows the compositions to be packaged in a dispensing container suitable for sale to and use by consumers (i.e., consumer packaging). In one embodiment, the composition is packaged in a squeeze bottle or hand pump container. The volume of the container may be greater than or equal to 25 ml, 50 ml, 100 ml and/or less than 1000 ml, 500 ml, or 250 ml, or within a range of the forgoing.

In some embodiments, the formation of the emulsion can be determined using a particle size analyzer and/or by measuring polydispersity. In one embodiment, the emulsion has a polydispersity index of less than 0.8, 0.7, 0.6 or 0.5. Where particle size of the hyaluronan needs to be measured, the measurement can be made by extracting hyaluronic acid particles using an extraction solvent such as hexane. Alternatively, the size of nanoparticles may be measured using TEM or SEM.

IV. Dermatological Compositions

Figure 1:
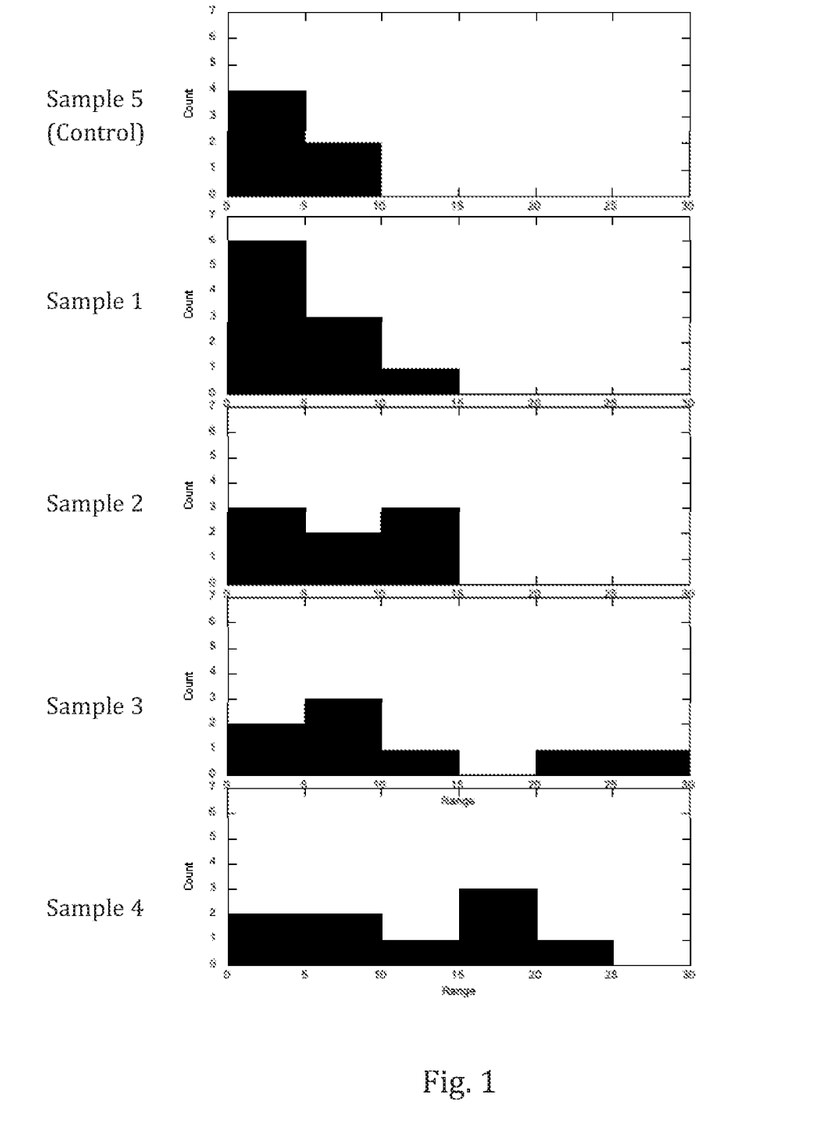
FIG. 1 shows transdermal delivery of hyaluronic acid in samples of dermatological compositions prepared using different emulsifiers and homogenization techniques.

The water-in-oil emulsion is formulated into a biocompatible ointment that can be applied to the skin of a person. The ointment may be a cream, foam, paste, gel, or the like. The ointment includes reverse micelles stably dispersed in a continuous oil phase. The dispersed reverse micelles have a particle size sufficiently small to migrate through the dermis. Forming nano-sized reverse micelle particles was found to have a surprisingly large impact on delivery of the hydrophilic component into or through the dermis. Water-soluble compounds that partition into the aqueous phase of the reverse micelle can be delivered to the subdermal layers of skin.

This is in contrast to traditional dermatological products, which use an oil-in-water emulsion. The oil-in-water emulsion creates oil particles that are held on the surface of the skin by the aqueous phase. Because the aqueous phase is the continuous phase, it does not penetrate the skin. Instead, the aqueous phase evaporates and leaves an oily-surfactant residue. While this residue can inhibit water from leaving the skin, it typically does a poor job of infusing water and other hydrophilic components into the skin. The compositions of the present invention overcome these deficiencies using transdermal delivery of properly sized hydrophilic micelles emulsified in a biocompatible continuous oil phase.

To achieve transdermal delivery of the reverse micelles, the median particle size may be less than 800 nm, 500 nm, 300 nm, or 150 nm and/or greater than 10 nm, 20 nm, 50 nm, 100 nm, 150 nm or in a range of any of the foregoing upper and lower particle sizes.

The emulsifiers, oil component, and their concentrations are selected to form reverse micelles. The emulsifier has a concentration in the oil phase that is above its critical micelle concentration. The emulsifier may be a single emulsifier or a plurality of emulsifiers so long as together the emulsifiers form micelles when dispersed in the oil phase.

The oils are selected to both disperse the reverse micelles and provide a desired amount of viscosity. The viscosity may be a thick cream (non-flowable) to a water-thin emulsion (flowable liquid) or a foam. The composition preferably includes an oil selected from essential and/or non-essential fatty acid, wax, or a butter. The oil may be saturated or unsaturated. The use of essential fatty acids can be advantageous for skin repair. Since the reverse micelles are delivered into the dermis, the use of essential and/or non-essential fatty acids in the compositions of the present invention have a more potent effect than fatty acids that are included in a traditional oil in water emulsion.

One of the most important aspects of dermatological products in general, and cosmetic products in particular, is the consumer's perception of the aesthetic qualities of a product. For example, while white petrolatum is an excellent moisturizer and skin protectant, it is rarely used alone, especially on the face, because it is greasy, sticky, does not rub easily into the skin and may soil clothing. Consumers highly value products which are aesthetically elegant and have an acceptable tactile feel and performance on their skin.

The oils of the continuous phase are selected to produce a composition that is non-oily when applied to the skin. Selecting oils that have esters and/or fatty acids facilitates this important characteristic.

The present invention also includes methods of using the compositions described herein. In one embodiment the method includes (i) identifying a person in need of treatment of the skin, (ii) providing a biocompatible topical skin ointment that includes reverse micelles dispersed in an oil-based continuous phase, and (iii) applying the topical skin ointment to the skin of a person. The compositions may be used to treat dry skin or eczema, or to facilitate repair of the dermis or other components of the skin.

V. Examples

Example 1

Example 1 describes the preparation of 5 samples that illustrate the benefits of forming reverse micelles and using a low molecular weight emulsifier and sonication to form nano-sized reverse micelle particles. Example 1 describes the preparation of five samples. Sample 4 is the only sample to include nanoparticle reverse micelles formed from a low molecular emulsifier and sonication.

A stock of 0.86% HA-FITC was created by dissolving 0.5 g of HA-FITC into a solution of 55.5 ml of water and 2.9 g of other ingredients (pH adjustors, thickeners, and aesthetic enhancers).

This stock was diluted to a total concentration of 0.5% HA-FITC by combining it in a final formulation (water-in-oil): (i) 30% oil (mixture of $>C_{15}$ fatty acid and ester oil unsaturated hydrocarbons), (ii) 10% emulsifiers; (iii) 1% preservative (iv) 59% stock solution described above.

Four samples were created by varying the type of emulsifiers (high molecular weight vs low molecular weight) and by varying the mixing method for emulsification (high shear mixing vs. sonication).

Sample 1: Polymeric Emulsifiers and High Sheer Mixing

Sample 1 was prepared by mixing the stock solution with polymeric emulsifiers having a molecular weight in a range between 2-3 kDa to form a precursor mixture. The precursor mixture was mixed using high shear mixing to create an emulsion.

Sample 2: Low Molecular Weight Emulsifier and High Sheer Mixing

Sample 2 was prepared by mixing the stock solution with span/tween emulsifiers to form a precursor mixture. The precursor mixture as mixed using high sheer mixing to create an emulsion.

Sample 3: Polymeric Emulsifier and Sonication

Sample 3 was prepared using the same emulsifiers as Sample 1 (i.e., polymeric), but the precursor mixture was mixed using sonic homogenization instead of high shear mixing.

Sample 4: Low Molecular Weight Emulsifier and Sonication

Sample 4 was prepared using the same emulsifiers as Sample 2 (i.e., tween/spa, but the precursor mixture was mixed using sonic homogenization instead of high shear mixing.

Sample 5: Control

Sample 5 was created by using 10 g of a commercially available oil-in-water emulsion as a base (dimethicone/petroleum), and adding 50 mg of HA-FITC with mixing. Sample 5 provides a control showing transdermal delivery of a hydrophilic material using a commercially available lotion.

The samples were then tested for transdermal delivery of the fluorescently labeled hyaluronic acid. 0.1 g of cream was added to a reservoir of a modified Franz diffusion cell. Cadaver skin was placed on top with the outside of the skin facing the cream. A chamber well fixed the skin sample in place, and 200 μl of PBS was placed in the chamber well. After varying time points (day to several days), the chamber well samples were withdrawn and read in a fluorometer. A standard curve was used to convert the FSU fluorometer units to concentration of HA-FITC in the sample.

FIG. 1 shows the results of the transdermal test for samples 1-5 (control sample 5 is shown on top, range is ng hyaluronic acid transported across the skin per cm per hour). As seen in the data, sample 1 lacks any substantial improvement over control sample 5. Samples 2-4 show improved transdermal delivery of hydrophilic compounds when the emulsifier and the mixing technique are selected to produce nanoparticle sized reverse micelles with a low molecular weight emulsifier. There is a detectable shift in the peak of the histogram confirmed by mood's median stats test. The emulsifier system and processing independently double the skin penetration rate (samples 2 and 3). As shown by sample 4, using sonication and a low molecular weight emulsifier together has a synergistic improvement in which the rate of transdermal delivery is quadrupled over the standard emulsifier systems and processing used in the skin care industry (dimethicone/petroleum based and high sheer mixing).

Figure 2:
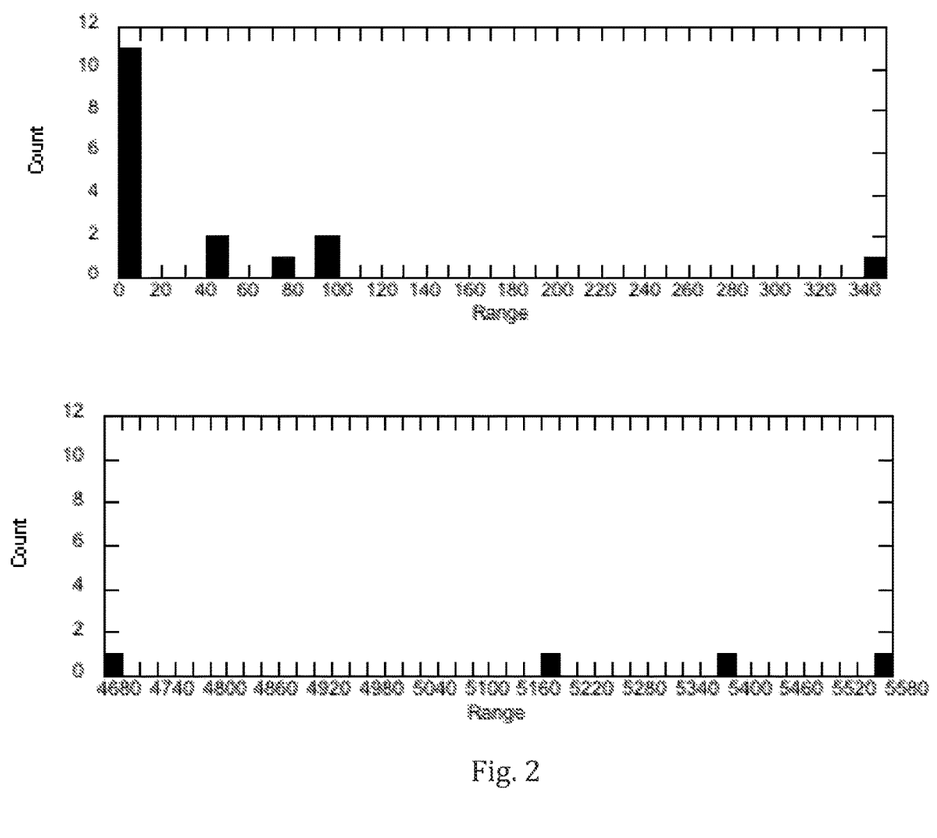
FIG. 2 is a peak histogram of micelle particle size in Sample 4 of Example 1.

Sample 4 was further analyzed using a particle size analyzer to confirm the presence and size of the micelles. FIG. 2 is a peak histogram (in nanometers) showing that most of the particles are between 0 and 100 nanometers and that the particle sizes are polydisperse.

Sample 4 was further tested by applying it to the skin of test subjects and measuring the conductance of the skin to determine whether the skin had improved moisture content. Volunteers were given two products labeled "A" and "B". Product A was the test composition of Sample 4 and Product B was the commercially available silicone-based product of Sample B (i.e., the control). The volunteers were instructed to apply one product to one side of the body and the other product to the opposite of the body each night for 10 days.

Figure 3:
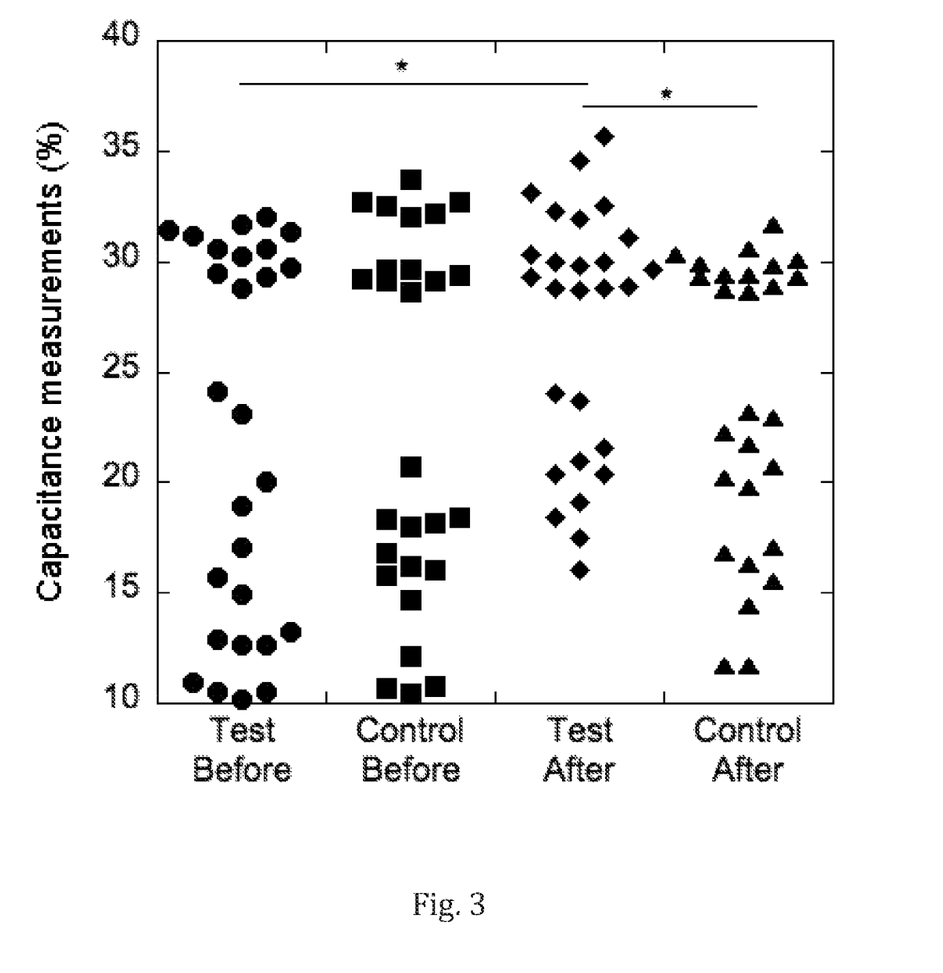
FIG. 3 shows the results of a capacitance test on skin treated with a control and the composition of Sample 4.

Prior to application of the creams, a skin capacitance device was used to take baseline measurements. Following daily application of Products A and B over the 10 day period, a second measurement of skin capacitance was taken. FIG. 2 shows the results of the capacitance measurements before and after applying Products A and B. As shown in FIG. 3, Product A, prepared according to the present invention (labeled "Test"), had a statistically significant increase in the skin capacitance measurements before and after application as compared to the control before and after application. The increased capacitance is indicative of an increase in moisture in the skin due to the topical treaty rent of using Sample 4 prepared according to one embodiment of the present invention.

VI. Definitions

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or" as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by e "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus; as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United. States Patent Office Manual of Patent Examining Procedures, Section 2111.03.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for making a dermatological composition, comprising:
   forming a dermatological precursor composition comprising (i) a biocompatible oil, (ii) an aqueous component including a humectant, emollient, or water-soluble active agent, (iii) an emulsifier having a molecular weight less than 2 kDa, wherein the concentration of the emulsifier in the biocompatible oil exceeds the critical micelle concentration, (iv) a film forming agent, and (v) a viscosity modifier; and
   mixing the dermatological precursor composition with a sheer force sufficient to form a dermatological mixture comprising reverse micelles having a median particle size less than 800 nm in diameter.

2. The method of claim 1, wherein the mixing is carried out using sonic homogenization.

3. The method of claim 1, wherein the mixing is carried out to form reverse micelles with a median particle size of less than 500 nm.

4. The method of claim 1, wherein the biocompatible oil includes lipid molecules with a carboxylic acid group, an ester group, and/or an ether group.

5. The method of claim 4, wherein the biocompatible oil includes a lipid with a hydrocarbon chain length in a range from 8-20 carbons.

6. The method of claim 1, wherein the emulsifier includes a nonionic compound.

7. The method of claim 1, wherein the emulsifier includes a polysorbate, sorbitan, or a combination thereof.

8. The method of claim 1, wherein the precursor composition includes a film forming agent.

9. The method of claim 8, wherein the film forming agent includes a crosslinked siloxane formed by the reaction of an ethenyl-terminated siloxane and methylhydroxydimethyl siloxane in the presence of cyclomethicone.

10. The method of claim 1, further comprising forming a topical skin emulsion comprising a cream, a foam, a paste, or a gel, the topical skin emulsion including at least a portion of the reverse micelles of claim 1.

11. The method of claim 10, further comprising stabilizing the reverse micelles in the topical skin emulsion using a preservative in sufficient quantity to stabilize the reverse micelles at room temperature for at least ten days and placing the topical skin emulsion in a consumer packaging.

12. The method of claim 1, wherein the precursor includes a humectant comprising hyaluronan and the reverse micelles form with the hyaluronan in a hydrophilic component thereof.

13. The method of claim 12, wherein the hyaluronan has a molecular weight in a range from 7,000-15,000 Daltons.

14. The method of claim 12, wherein the hydrophilic component includes a water-soluble pharmaceutically active agent.

15. A method for making a dermatological composition, comprising:
   forming a dermatological precursor composition comprising (i) a biocompatible oil, (ii) an aqueous component including a humectant, emollient, or water-soluble active agent, (iii) a film forming agent, and (iv) a non-ionic emulsifier having a molecular weight less than 2 kDa, wherein the concentration of the emulsifier in the biocompatible oil exceeds the critical micelle concentration;
   mixing the dermatological precursor composition with sufficient sonic homogenization to form a mixture comprising reverse micelles in a continuous phase of the biocompatible oil, the micelles having a median particle size less than 500 nm in diameter;
   forming a topical skin emulsion comprising a cream, a foam, a paste, or a gel, the topical skin emulsion including at least a portion of the reverse micelles.

16. The method of claim 15, wherein:
   the emulsifier includes polysorbate, sorbitan, or a combination thereof;
   the precursor includes a hydrophilic component selected from a humectant, emollient, or water-soluble active agent; and
   the film forming agent includes a crosslinked siloxane formed by the reaction of an ethenyl-terminated siloxane and methylhydroxydimethyl siloxane in the presence of cyclomethicone.

17. The method of claim 15, wherein the biocompatible oil includes lipid molecules with a carboxylic acid group, an ester group, and/or an ether group and having a hydrocarbon chain length in a range from 8-20 carbons.

18. The method of claim 15, wherein the precursor composition includes a humectant comprising hyaluronan with a molecular weight in a range from 7,000-15,000 Daltons, and the reverse micelles form with the hyaluronan in a hydrophilic component thereof.

19. A method for treating a skin condition, comprising identifying a patient with a skin condition and applying to the skin thereof the reverse micelles formed according to the method of claim 1.

* * * * *